United States Patent
Ishii et al.

(10) Patent No.: US 8,658,840 B2
(45) Date of Patent: Feb. 25, 2014

(54) METHOD FOR PRODUCING β-FLUOROALCOHOL

(75) Inventors: Akihiro Ishii, Kawagoe (JP); Takashi Ootsuka, Kawagoe (JP); Takehisa Ishimaru, Kawagoe (JP); Mari Imamura, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/990,114

(22) PCT Filed: Jan. 27, 2012

(86) PCT No.: PCT/JP2012/051765
§ 371 (c)(1),
(2), (4) Date: May 29, 2013

(87) PCT Pub. No.: WO2012/105431
PCT Pub. Date: Aug. 9, 2012

(65) Prior Publication Data
US 2013/0303774 A1 Nov. 14, 2013

(30) Foreign Application Priority Data

Feb. 3, 2011 (JP) ................. 2011-021355
Mar. 1, 2011 (JP) ................. 2011-043916
May 27, 2011 (JP) ................. 2011-119137
Aug. 2, 2011 (JP) ................. 2011-168992
Jan. 12, 2012 (JP) ................. 2012-003743

(51) Int. Cl.
*C07C 31/38* (2006.01)
*C07F 15/00* (2006.01)

(52) U.S. Cl.
USPC ........................... 568/842; 556/21

(58) Field of Classification Search
USPC ........................... 568/842; 556/21
See application file for complete search history.

(56) References Cited

U.S. PATENT DOCUMENTS

| | | | |
|---|---|---|---|
| 4,761,506 | A | 8/1988 | Cordier et al. |
| 7,462,734 | B2 | 12/2008 | Ishii et al. |
| 7,569,735 | B2 | 8/2009 | Ino et al. |
| 7,989,665 | B2 | 8/2011 | Saudan et al. |
| 8,124,816 | B2 | 2/2012 | Saudan et al. |
| 8,344,187 | B2 | 1/2013 | Ikariya et al. |
| 2011/0237814 | A1 | 9/2011 | Kuriyama et al. |

FOREIGN PATENT DOCUMENTS

| | | |
|---|---|---|
| JP | 61-171448 A | 8/1986 |
| JP | 8-3086 A | 1/1996 |
| JP | 2006-83163 A | 3/2006 |
| JP | 2008-260758 A | 10/2008 |
| JP | 2008-537946 A | 10/2008 |
| JP | 2010-37329 A | 2/2010 |
| WO | WO 2006/106484 A1 | 10/2006 |
| WO | WO 2007/093567 A1 | 8/2007 |
| WO | WO 2011/048727 A1 | 4/2011 |

OTHER PUBLICATIONS

Corresponding International Search Report with English Translation dated Mar. 27, 2012 (six (6) pages).
Japanese-language Written Opinion dated Mar. 27, 2012 (PCT/ISA/237) (three (3) pages).
Mohammed S. Rahman et al., "Coordination Chemistry and Catalytic Activity of Ruthenium Complexes of Terdentate Phosphorus-Nitrogen-Phosphorus (PNP) and Bidentate Phosphorus-Nitrogen (PHN) Ligands", Organometallics, vol. 21, 2002, pp. 4927-4933.
Theodora W. Greene et al., "Protective Groups in Organic Synthesis", 3rd edition, 1999, John Wiley & Sons, Inc., (twenty-eight (28) pages).
L. S. Hegedus, "Transition Metals in the Synthesis of Complex Organic Molecules", 2nd edition, Tokyo Kagaku Dojin, 2001, (eight (8) pages).
Ryoji Noyori et al., "Organic Chemistry for Graduate Students vol. II: Molecular Structure & Reaction/Organic Metal Chemistry", Tokyo Kagaku Dojin, 1999, (five (5) pages).
Matthew L. Clarke et al., "Hydrogenation of Aldehydes, Esters, Imines, and Ketones Catalyzed by a Ruthenium Complex of a Chiral Tridentate Ligand", Organometallics, vol. 26, No. 1, 2007, pp. 16-19.
Wataru Kuriyama et al., "A Homogeneous Catalyst for Reduction of Optically Active Esters to the Corresponding Chiral Alcohols without Loss of Optical Purities", Adv. Synth. Catal., vol. 352, 2010, pp. 92-96.

*Primary Examiner* — Charanjit Aulakh
(74) *Attorney, Agent, or Firm* — Crowell & Moring LLP

(57) ABSTRACT

A production method of a β-fluoroalcohol includes performing a reaction of an α-fluoroester with hydrogen gas ($H_2$) in the presence of a specific ruthenium complex (i.e. a ruthenium complex of the general formula [2], preferably a ruthenium complex of the general formula [4]). This production method can employ a suitable hydrogen pressure of 1 MPa or less by the use of such a specific ruthenium complex and does not require a high-pressure gas production facility when put in industrial practice. In addition, this production method can remarkably reduce the amount of catalyst used therein (to e.g. a substrate/catalyst ratio of 20,000) in comparison to the substrate/catalyst ratio conventional reduction of α-fluoroalcohol. It is possible by these reduction in hydrogen pressure and catalyst amount to largely reduce the production cost of the β-fluoroalcohol.

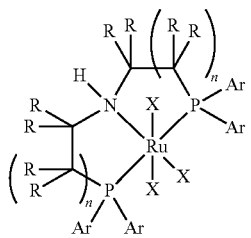

[2]

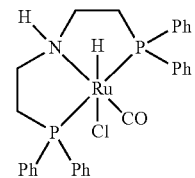

[4]

8 Claims, No Drawings

METHOD FOR PRODUCING β-FLUOROALCOHOL

TECHNICAL FIELD

The present invention relates to a method for industrial production of a β-fluoroalcohol.

BACKGROUND ART

β-fluoroalcohols can be produced by reduction of corresponding α-fluoroesters. For such reduction reactions, it is often to use stoichiometric amounts of hydride reducing agents such as lithium aluminum hydride (see Patent Document 1 and Scheme 1). However, the processes for producing β-fluoroalcohols with the use of stoichiometric amounts of hydride reducing agents are not suitable for mass-scale production due to the facts that: the reducing agents are expensive and require caution in handling; and the after-treatment of the resulting reaction products requires complicated operations and causes large amounts of wastes.

Scheme 1

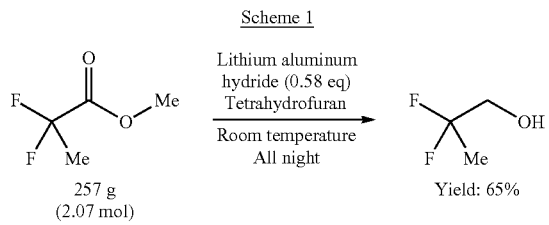 [SMILES: COC(=O)C(C)(F)F ; CC(F)(F)CO]

On the other hand, there have been reported processes for producing alcohols by reaction of esters with hydrogen gas ($H_2$) in the presence of ruthenium catalysts (see Patent Documents 2 to 4 and Non-Patent Document 1).

PRIOR ART DOCUMENTS

Patent Documents

Patent Document 1: Japanese Laid-Open Patent Publication No. 2006-083163
Patent Document 2: International Application Publication No. 2006/106484
Patent Document 3: U.S. Pat. No. 7,569,735
Patent Document 4: Japanese Laid-Open Patent Publication No. 2010-037329

Non-Patent Documents

Non-Patent Document 1: Adv. Synth. Catal. (Germany), 2010, vol. 352, p. 92-96

SUMMARY OF THE INVENTION

Problems to be Solved by the Invention

The processes for producing β-fluoroalcohols by reaction of α-fluoroesters with hydrogen gas in the presence of ruthenium catalysts provide solutions to all of the problems in the use of stoichiometric amounts of hydride reducing agents, but result in high cost because these processes require a high hydrogen pressure of the order of 5 MPa and thus need to be industrially performed in high-pressure gas production facilities.

It is accordingly an object of the present invention to find out a catalyst (or catalyst precursor) capable of reducing a hydrogen pressure in the reduction reaction of an α-fluoroester with hydrogen and thereby provide a method for industrial production of a β-fluoroaclohol by reduction of an α-fluoroester with hydrogen by the use of such a catalyst.

Means for Solving the Problems

The present inventors have made extensive researches in view of the above problems and, as a result, have found that: a ruthenium complex of the general formula [2], notably a ruthenium complex of the general formula [4], is capable of dramatically reducing a hydrogen pressure in the hydrogen reduction reaction of an α-fluoroester.

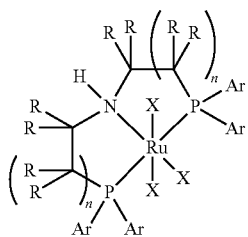

[2]

In the general formula [2], R each independently represent a hydrogen atom, an alkyl group, a substituted alkyl group, an aromatic ring group or a substituted aromatic ring group; Ar each independently represent an aromatic ring group or a substituted aromatic ring group; X each independently represent a ligand having a formal charge of −1 or 0 (with the proviso that the sum of formal charges of three X is −2); and n each independently represent an integer of 1 or 2.

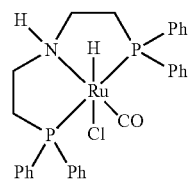

[4]

In the formula [4], Ph represent a phenyl group.

Even in the case of using the above ruthenium complex, the hydrogen reduction of an ester having no fluorine atom at its α-position needs a hydrogen pressure of 4 to 5 MPa (see Comparative Example 2 explained later). On the other hand, the hydrogen reduction of an α-fluoroester needs a hydrogen pressure of about 5 MPa even in the case of using any other ruthenium complex analogous to the above ruthenium complex (see Comparative Example 1 explained later as well as Example 26 of Patent Document 4). As a matter of course, there remains a need to set a high hydrogen pressure in the hydrogen reduction using an ester having no fluorine atom at its α-position in combination with the other analogous ruthenium complex. It is possible to obtain a dramatic effect (dramatic reduction of hydrogen pressure in reduction reaction) only by the combined use of the ruthenium complex of the general formula [2], notably ruthenium complex of the general formula [4], and the α-fluoroester.

In this way, the present inventors have found useful techniques for industrial production of β-fluoroalcohols. The present invention is based on these findings.

Namely, the present invention provides a method for producing a β-fluoroalcohol according to Inventive Aspects 1 to 8.

[Inventive Aspect 1]

A method for producing a β-fluoroalcohol of the general formula [3], comprising: performing a reaction of an α-fluoroester of the general formula [1] with hydrogen gas (H$_2$) in the presence of a ruthenium complex of the general formula [2]

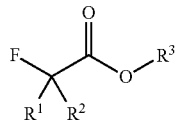

[1]

where R$^1$ and R$^2$ each independently represent a hydrogen atom, a halogen atom, an alkyl group, a substituted alkyl group, an aromatic ring group, a substituted aromatic ring group, an alkoxycarbonyl group or a substituted alkoxycarbonyl group; and R$^3$ represents an alkyl group or a substituted alkyl group

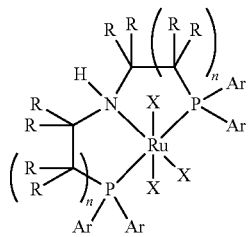

[2]

where R each independently represent a hydrogen atom, an alkyl group, a substituted alkyl group, an aromatic ring group or a substituted aromatic ring group; Ar each independently represent an aromatic ring group or a substituted aromatic ring group; X each independently represent a ligand having a formal charge of −1 or 0 (with the proviso that the sum of formal charges of three X is −2); and n each independently represent an integer of 1 or 2

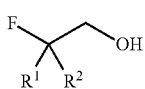

[3]

where R$^1$ and R$^2$ have the same definitions as in the general formula [1].

[Inventive Aspect 2]

The method according to Inventive Aspect 1, wherein the reaction is performed in the presence of a base.

[Inventive Aspect 3]

A method for producing a β-fluoroalcohol of the general formula [3], comprising: performing a reaction of an α-fluoroester of the general formula [1] with hydrogen gas (H$_2$) in the presence of a ruthenium complex of the general formula [4] and a base

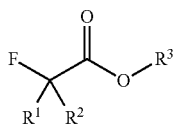

[1]

where R$^1$ and R$^2$ each independently represent a hydrogen atom, a halogen atom, an alkyl group, a substituted alkyl group, an aromatic ring group, a substituted aromatic ring group, an alkoxycarbonyl group or a substituted alkoxycarbonyl group; and R$^3$ represents an alkyl group or a substituted alkyl group

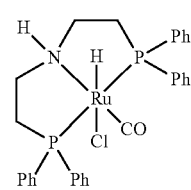

[4]

where Ph represent a phenyl group

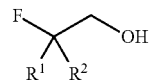

[3]

where R$^1$ and R$^2$ have the same definitions as in the general formula [1].

[Inventive Aspect 4]

The method according to any one of Inventive Aspects 1 to 3, wherein the α-fluoroester of the general formula [1] is an α-fluoroester of the general formula [5]; and wherein the β-fluoroalcohol of the general formula [3] is a β-fluoroalcohol of the general formula [6]

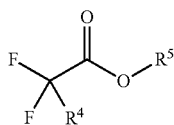

[5]

where R$^4$ represents a hydrogen atom, an alkyl group, a substituted alkyl group, an aromatic ring group or a substituted aromatic ring group; and R$^5$ represents an alkyl group

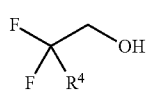

[6]

where R$^4$ has the same definition as in the general formula [5].

[Inventive Aspect 5]

The method according to any one of Inventive Aspects 1 to 3, wherein the α-fluoroester of the general formula [1] is an α-fluoroester of the general formula [7]; and wherein the β-fluoroalcohol of the general formula [3] is a β-fluoroalcohol of the general formula [8]

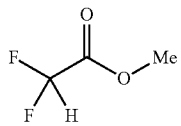

[7]

where Me represents a methyl group

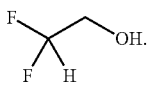

[8]

[Inventive Aspect 6]

The method according to any one of Inventive Aspects 1 to 5, wherein the reaction is performed at a hydrogen pressure of 3 MPa or lower.

[Inventive Aspect 7]

The method according to any one of Inventive Aspects 1 to 5, wherein the reaction is performed at a hydrogen pressure of 2 MPa or lower.

[Inventive Aspect 8]

The method according to any one of Inventive Aspects 1 to 5, wherein the reaction is performed at a hydrogen pressure of 1 MPa or lower.

In the present invention, the hydrogen pressure can preferably be set to 1 MPa or lower in the production of the β-fluoroalcohol by hydrogen reduction of the α-fluoroester at a hydrogen pressure of 1 MPa or lower. This eliminates the need to utilize a high-pressure gas production facility for the industrial production of the β-fluoroalcohol. The amount of the catalyst used can also be reduced to a significantly low level (e.g. to a substrate/catalyst ratio of 20,000) as compared to the substrate/catalyst ratio (of e.g. 1,000) in conventional reduction of α-fluoroalcohol. It is possible by these reductions in hydrogen pressure and catalyst amount to largely reduce the production cost of the β-fluoroalcohol. Further, the reduction reaction is inert to unsaturated bonds (such as carbon-carbon double bond) in the present invention so that it is a preferred embodiment of the present invention to carry out the reduction reaction in a functional-group-selective manner (see Examples 7 and 8 explained later).

DETAILED DESCRIPTION OF THE EMBODIMENTS

Hereinafter, the industrial production method of β-fluoroalcohol according to the present invention will be described in detail below. It is understood that: the scope of the present invention is not limited to the following examples; and various modifications and variations can be made to the following examples without departing from the scope of the present invention. All of the publications cited in the present specification, such as prior art documents and patent documents e.g. published patents and patent applications, are herein incorporated by reference. In the following description, the specific structures of the general formulas [1] to [8] are as indicated above.

In the present invention, the β-fluoroalcohol of the general formula [3] is produced by reaction of the α-fluoroester of the general formula [1] with hydrogen gas in the presence of the ruthenium complex of the general formula [2].

In the α-fluoroester of the general formula [1], $R^1$ and $R^2$ each independently represent a hydrogen atom, a halogen atom, an alkyl group, a substituted alkyl group, an aromatic ring group, a substituted aromatic ring group, an alkoxycarbonyl group or a substituted alkoxycarbonyl group. Examples of the halogen atom are fluorine, chlorine, bromine and iodine. Examples of the alkyl group are those of 1 to 18 carbon atoms having a straight-chain structure, a branched structure or a cyclic structure (in the case of 3 or more carbons). Examples of the aromatic ring group are those of 1 to 18 carbon atoms, such as: aromatic hydrocarbon groups as typified by phenyl, naphthyl and anthryl; and aromatic heterocyclic groups containing heteroatoms e.g. as nitrogen, oxygen or sulfur as typified by pyrrolyl (including nitrogen-protected form), pyridyl, furyl, thienyl, indolyl (including nitrogen-protected form), quinolyl, benzofuryl and benzothienyl. Examples of alkyl (R) of the alkoxycarbonyl group (ROCO) are the same as those of the above alkyl group. Examples of the substituted alkyl group, the substituted aromatic ring group and the substituted alkoxycarbonyl group are those obtained by substitution of any number of and any combination of substituents onto any of carbon or nitrogen atoms of the above alkyl, aromatic ring and alkoxycarbonyl groups. As such substituent groups, there can be used: halogen atoms such as fluorine, chlorine and bromine; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; cyano group; lower alkoxycarbonyl groups such as methoxycarbonyl, ethoxycarbonyl and propoxycarbonyl; aromatic ring groups such as phenyl, naphthyl, anthryl, pyrrolyl (including nitrogen-protected form), pyridyl, furyl, thienyl, indolyl (including nitrogen-protected form), quinolyl, benzofuryl and benzothienyl; carboxyl group; protected carboxyl groups; amino group; protected amino groups; hydroxyl group; and protected hydroxyl groups. The substituted alkyl group may be one obtained by substitution of an arbitrary carbon-carbon single bond or bonds of the alkyl group with any number of and any combination of carbon-carbon double bonds and carbon-carbon triple bonds. (The alkyl group with such an unsaturated bond may naturally have any of the above substituent groups. In the present specification, the alkyl group with the unsaturated bond is also categorized in the substituted alkyl group.) Depending on the kind of the substituent group, the substituent group itself may be involved in a side reaction. However, the side reaction can be minimized by the adoption of suitable reaction conditions. In the present specification, the term "lower" means that the group to which the term is attached is a group of 1 to 6 carbon atoms having a straight-chain structure, a branched structure or a cyclic structure (in the case of 3 or more carbons). The aromatic ring groups described above as "such substituent groups" may further be substituted with a halogen atom, a lower alkyl group, a lower haloalkyl group, a lower alkoxy group, a lower haloalkoxy group, a cyano group, a lower alkoxycarbonyl group, a carboxyl group, a protected carboxyl group, an amino group, a protected amino group, a hydroxyl group, a protected hydroxyl group etc. As the protecting groups of the pyrrolyl, indolyl, carboxyl, amino and hydroxyl groups, there can be used those described in "Protective Groups in Organic Synthesis", Third Edition, 1999, John Wiley & Sons, Inc. Among others, it is preferable that: either one of $R^1$ and $R^2$ is a fluorine atom; and the other of $R^1$ and $R^2$ is a hydrogen atom, an alkyl group, a substituted alkyl group, an aromatic ring group or a substituted aromatic ring group, more preferably a hydrogen atom.

Further, $R^3$ represents an alkyl group or a substituted alkyl group in the α-fluoroester of the general formula [1]. Examples of the alkyl and substituted alkyl groups as $R^3$ are the same as those of $R^1$ and $R^2$ in the α-fluoroester of the general formula [1]. Among others, alkyl is preferred. Particularly preferred is methyl.

The α-fluoroester of the general formula [5] is one preferred example of the α-fluoroester of the general formula [1]. Among others, the α-fluoroester of the general formula [7] is a particularly preferred example. The α-fluoroester of the general formula [5] is relatively readily available on a mass scale. The α-fluoroester of the general formula [7] is particularly preferred because the β-fluoroalcohol of the general formula [8] obtained from the α-fluoroester of the general formula [7] is important as an intermediate for pharmaceutical and agrichemical products.

In the case where the α-fluoroester of the general formula [1] has an asymmetric carbon atom at its α-position, the asymmetric carbon atom can be in any configuration (R-configuration, S-configuration or racemic configuration). When the optically active substance is used as the raw substrate material, the configuration of the target compound can be maintained, with almost no deterioration in optical purity, by the adoption of suitable reaction conditions (e.g. by "reacting in the absence of a base" as will be explained later or "slowly dropping the raw substrate material" as will be explained later in Example 12).

It is feasible to use α-fluorolactone as the raw substrate material in the present invention. Not only α-fluorolactone, but also any other compound capable of being converted to the target α-fluoroester by the action of the base or reaction solvent and then subjected to reduction reaction in the reaction system, are herein included in the scope of the present invention.

In the ruthenium complex of the general formula [2], R each independently represent a hydrogen atom, an alkyl group, a substituted alkyl group, an aromatic ring group or a substituted aromatic ring group. Examples of the alkyl, substituted alkyl, aromatic ring and substituted aromatic ring groups as R are the same as those of $R^1$ and $R^2$ in the α-fluoroester of the general formula [1]. Two vicinal R (except hydrogen atoms) may form a cyclic structure by covalent bond of carbon atoms through or without a nitrogen atom, an oxygen atom or a sulfur atom. It is preferable that all of eight R are hydrogen (each of two n is 1)

Ar each independently represent an aromatic ring group or a substituted aromatic ring group in the ruthenium complex of the general formula [2]. Examples of the aromatic ring or substituted aromatic ring groups as Ar are the same as those of $R^1$ and $R^2$ in the α-fluoroester of the general formula [1]. It is preferable that all of four Ar are phenyl.

X each independently represent a ligand having a formal charge of −1 or 0 with the proviso that the sum of formal charges of three X is −2 (the formal charge of Ru is +2) in the ruthenium complex of the general formula [2]. Examples of the ligand having a formal charge of −1 or 0 are: ligands described in "Hegedus: Transition Metals in the Synthesis of Complex Organic Molecules (written by L. S. Hegedus, Second Edition, translated by Shinji Murai, p. 4-9, Tokyo Kagaku Dojin, 2001)" and in "Organic Chemistry for Graduate Students Vol. II: Molecular Structure & Reaction/Organic Metal Chemistry (Ryoji Noyori et al., p. 389-390, Tokyo Kagaku Dojin, 1999)" etc.; $BH_4^-$; and $R^6CO_2^-$. (Herein, $R^6$ represents a hydrogen atom, an alkyl group or a substituted alkyl group. Examples of the alkyl and substituted alkyl groups as $R^6$ are the same as those of $R^1$ and $R^2$ in the α-fluoroester of the general formula [1].) Among others, it is preferable that the three ligands are hydrogen, chlorine and carbon monoxide, respectively.

The reaction can be performed in the absence of the base in the case where at least one of three X ligands is $BH_4$ in the ruthenium complex of the general formula [2]. (As a matter of course, it is alternatively feasible to perform the reaction in the presence of the base). Among others, it is preferable to use the ruthenium complex of the general formula [4] in which the Cl ligand has been replaced by $BH_4(H—BH_3)$ (see International Application Publication No. 2011/048727).

Further, n each independently represent an integer of 1 or 2 in the ruthenium complex of the general formula [2]. In the case where n is 1, a nitrogen atom and a phosphorus atom are bonded to each other via two carbon atoms in the ruthenium complex. In the case where n is 2, a nitrogen atom and a phosphorus atom are bonded to each other via three carbon atoms in the ruthenium complex. It is preferable that each of both two n is 2.

In the ruthenium complex of the general formula [4], Ph represent a phenyl group.

The ruthenium complex of the general formula [4] is one preferred example of the ruthenium complex of the general formula [2]. As the ruthenium complex of the general formula [4], there can be used a commercially available product "Ru-MACHO™" (manufactured by Takasago International Corporation).

It is feasible to prepare the ruthenium complex of the general formula [2] in a similar manner to that for preparation of Ru-MACHO™. Water or an organic solvent such as toluene may be contained in the ruthenium complex. It suffices that the purity of the ruthenium complex is 70% or higher. The purity of the ruthenium complex is preferably 80% or higher, more preferably 90% or higher.

It suffices to use the ruthenium complex of the general formula [2] in an amount of 0.000001 mol or more per 1 mol of the α-fluoroester of the general formula [1]. The amount of the ruthenium complex of the general formula [2] used is preferably 0.00001 to 0.005 mol, more preferably 0.00002 to 0.002 mol, per 1 mol of the α-fluoroester of the general formula [1].

Examples of the base usable in the reaction are: alkali metal hydrogencarbonates such as lithium hydrogencarbonate, sodium hydrogencarbonate and potassium hydrogencarbonate; alkali metal carbonates such as lithium carbonate, sodium carbonate and potassium carbonate; alkali metal hydroxides such as lithium hydroxide, sodium hydroxide and potassium hydroxide; tetraalkyl ammonium hydroxides such as tetramethyl ammonium hydroxide, tetraethyl ammonium hydroxide, tetra-n-propyl ammonium hydroxide and tetra-butyl ammonium hydroxide; alkali metal alkoxides such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide and potassium tert-butoxide; organic bases such as triethylamine, diisopropylethylamine, 4-dimethylaminopyridine and 1,8-diazabicyclo[5.4.0]undec-7-ene; alkali metal bis(trialkylsilyl)amides such as lithium bis(trialkylsilyl)amide, sodium bis(trialkylsilyl)amide and potassium bis(trialkylsilyl)amide; and alkali metal borohydrides such as lithium borohydride, sodium borohydride and potassium borohydrode. Among others, alkali metal alkoxides are preferred. Particularly preferred are lithium methoxide, sodium methoxide and potassium methoxide.

It suffices to use the base in an amount of 0.001 mol or more per 1 mol of the α-fluoroester of the general formula [1]. The amount of the base used is preferably 0.005 to 5 mol, more preferably 0.01 to 3 mol, per 1 mol of the α-fluoroester of the general formula [1].

As it is assumed that the true catalytic active species is derived from the ruthenium catalyst of the general formula [2] optionally in the presence of the base, the case where the catalytic active species (including isolated form) is prepared in advance and used in the reduction reaction is included in the scope of the present invention.

It suffices to use the hydrogen gas in an amount of 2 mol or more per 1 mol of the α-fluoroester of the general formula [1]. The hydrogen gas is preferably used in a large excessive amount, more preferably in a large excessive amount under the following pressurized conditions.

There is no particular limitation on the hydrogen pressure. The hydrogen pressure is preferably 3 to 0.001 MPa, more preferably 2 to 0.01 MPa. It is particularly preferred that the hydrogen pressure is 1 MPa or lower in order to maximize the effects of the present invention.

Examples of the reaction solvent usable in the reaction are: aliphatic hydrocarbon solvents such as n-hexane and n-heptane; aromatic hydrocarbon solvents such as toluene and xylene; halogenated solvents such as methylene chloride and 1,2-dichloroethane; ether solvents such as diethyl ether, 1,2-dimethoxyethane, 1,4-dioxane, tetrahydrofuran, 2-methyltetrahydrofuran, tert-butyl methyl ether, diisopropyl ether, diethylene glycol dimethyl ether and anisole; alcohol solvents such as methanol, ethanol, n-propanol, isopropanol, n-butanol, tert-butanol, n-pentanol, n-hexanol and cyclohexanol; amide solvents such as N,N-dimethylformamide and 1,3-dimethyl-2-imidazolidinone; nitrile solvents such as acetonitrile and propionitrile; and dimethyl sulfoxide. Among others, ether solvents and alcohol solvents are preferred. Alcohol solvents are more preferred as the reaction solvent. These reaction solvents can be used solely or in combination of two or more thereof. It is particularly preferable to use methanol, which is easy to separate by fractional distillation, for production of the β-fluoroalcohol of the general formula [8] as the preferred target compound.

It suffices to use the reaction solvent in an amount of 0.01 L (liter) or more per 1 mol of the α-fluoroester of the general formula [1]. The amount of the reaction solvent used is preferably 0.03 to 10 L, more preferably 0.05 to 7 L, per 1 mol of the α-fluoroester of the general formula [1]. The reaction can alternatively be performed under neat conditions without the use of the reaction solvent.

It suffices that the reaction temperature is +150° C. or lower. The reaction temperature is preferably +125 to −50° C., more preferably +100 to −25° C.

Further, it suffices that the reaction time is 72 hours or less. As the reaction time varies depending on the raw substrate material and reaction conditions, it is preferable to determine the time at which there is seen almost no decrease of the raw substrate material as the end of the reaction while monitoring the progress of the reaction by any analytical means such as gas chromatography, liquid chromatography or nuclear magnetic resonance.

The β-fluoroalcohol of the general formula [3] can be obtained by any ordinary post treatment operation for organic synthesis. In the case where $R^1$ and/or $R^2$ is alkoxycarbonyl or substituted alkoxycarbonyl in the α-fluoroester of the general formula [1], the reaction product may be in the form of a diol or triol (see Example 11). This reaction is also included in the scope of the present invention. Further, the crude product can be purified to a high purity, as needed, by activated carbon treatment, fractional distillation, recrystallization, column chromatography or the like. It is convenient to directly subject the reaction completed solution to distillation recovery operation in the case where the target compound has a low boiling point. In the case where the reaction is performed in the presence of the base, the target compound of relatively high acidity tends to form a salt or complex with the base used and remain in the distillation residue during distillation recovery operation. In such a case, the target compound can be obtained with high yield by neutralizing the reaction completed solution with an organic acid such as formic acid, acetic acid, citric acid, oxalic acid, benzoic acid, methanesulfonic acid or paratoluenesulfonic acid or an inorganic acid such as hydrogen chloride, hydrogen bromide, nitric acid or sulfuric acid in advance, and then, subjecting the neutralized reaction completed solution to distillation recovery operation (including recovery by washing the distillation residue with an organic solvent such as diisopropyl ether).

EXAMPLES

The present invention will be described in more detail below by way of the following examples. It should be noted that the following examples are illustrative and are not intended to limit the present invention thereto. In the present invention, α-fluoroesters can be produced as the raw substrate material in similar manners with reference to publicly known disclosures. (As a matter of course, it is feasible to use commercially available α-fluoroesters as the raw substrate material.) In particular, the raw substrate materials of the following Examples 7 and 8 can be produced with high yield by ordinary organic synthesis processes. For example, it is convenient to produce the α-fluoroester by the following steps: 1) Reformatsky reaction of bromodifluoroacetic acid ethyl ester and propionaldehyde or acetoaldehyde; 2) conversion of a hydroxyl group (—OH) to a trifluoromethanesulfonyl group (—OSO$_2$CF$_3$); and 3) elimination of a trifluoromethanesulfonic acid by a strong base. (The raw substrate material of the following Example 13 is the reaction product of the above step 1.) In the following description, the abbreviations "Me", "Ph", and "Et" refer to methyl, phenyl and ethyl, respectively.

Example 1

A pressure-proof reaction vessel of stainless steel (SUS) was charged with 4.4 g (40 mmol, 1 eq) of α-fluoroester of the following formula, 5.2 mg (purity: 94.2%; 8.0 mmol, 0.0002 eq) of ruthenium complex of the following formula, 540 mg (10 mmol, 0.25 eq) of sodium methoxide and 40 mL (1.0 L/mol) of methanol.

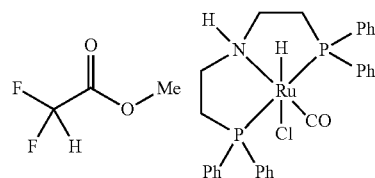

The inside of the reaction vessel was replaced five times with hydrogen gas. The hydrogen pressure inside the reaction vessel was then set to 1.0 MPa. The resulting solution inside the reaction vessel was stirred all night at 40° C. It was confirmed by gas chromatographic analysis of the reaction completed solution that the conversion rate and the selectivity of β-fluoroalcohol of the following formula were each 100%.

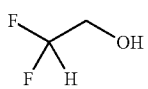

The reaction completed solution was directly subjected to distillation so that the target compound was recovered in the form of a methanol solution thereof. It was confirmed by $^{19}$F-NMR quantitative analysis of the methanol solution according to internal standard method (internal standard material: α,α,α-trifluorotoluene) that 3.0 g of the target compound was contained. The yield of the target compound was thus 91%. For reference purposes, the reaction procedure and reaction results of the present example are indicated in the following scheme.

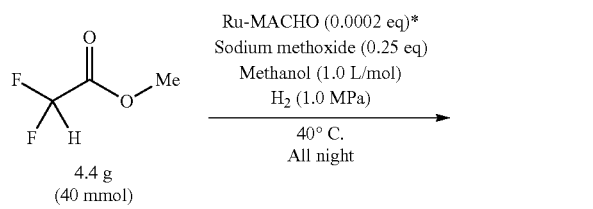

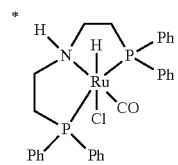

Example 2

A pressure-proof reaction vessel of stainless steel (SUS) was charged with 53 g (480 mmol, 1 eq) of α-fluoroester of the following formula, 15 mg (purity: 94.2%; 24 μmol, 0.00005 eq) of ruthenium complex of the following formula, 8.4 g (120 mmol, 0.25 eq) of potassium methoxide and 240 mL (0.5 L/mol) of methanol.

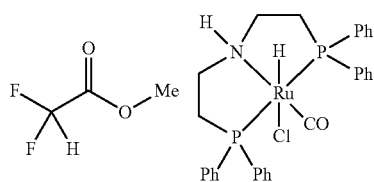

The inside of the reaction vessel was replaced five times with hydrogen gas. The hydrogen pressure inside the reaction vessel was then set to 1.0 MPa. The resulting solution inside the reaction vessel was stirred all night at 40° C. It was confirmed by gas chromatographic analysis of the reaction completed solution that the conversion rate and the selectivity of β-fluoroalcohol of the following formula were 100% and 97.6%, respectively.

For reference purposes, the reaction procedure and reaction results of the present example are indicated in the following scheme.

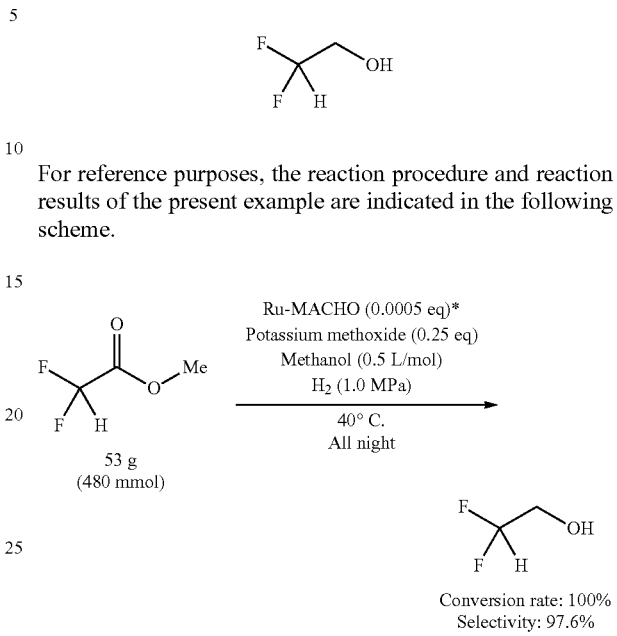

The above reaction operation was repeated five times to obtain the reaction completed solution equivalent to 2.4 mol of α-fluoroester. The reaction completed solution was admixed with 36 g (600 mmol, 0.25 eq) of acetic acid. The admixed solution was directly subjected to distillation (oil bath temperature: 55° C., vacuum degree: ~1.5 kPa) so that the target compound was recovered in the form of a methanol solution thereof. The distillation residue (i.e. the solid matter containing the target compound and potassium acetate) was washed by stirring with 200 mL of diisopropyl ether and filtered out. The resulting solid matter was further washed with 200 mL of diisopropyl ether. The target compound was thus recovered in the form of a diisopropyl ether solution thereof. The above recovered solutions were combined and subjected to distillation separation (theoretical plate number: 20, distillation temperature: 92° C., atmospheric pressure), thereby yielding 158 g of β-fluoroalcohol of the above formula. The yield of β-fluoroalcohol was 80%. The gas chromatographic purity of β-fluoroalcohol was 99.6%. The water content of β-fluoroalcohol was 0.05%.

Example 3

A pressure-proof reaction vessel of stainless steel (SUS) was charged with 4.2 g (40 mmol, 1 eq, optical purity 98.4% ee) of α-fluoroester of the following formula, 5.2 mg (purity: 94.2%; 8.0 μmol, 0.0002 eq) of ruthenium complex of the following formula, 700 mg (10 mmol, 0.25 eq) of potassium methoxide and 20 mL (0.5 L/mol) of methanol.

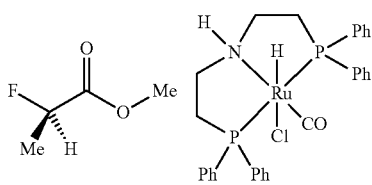 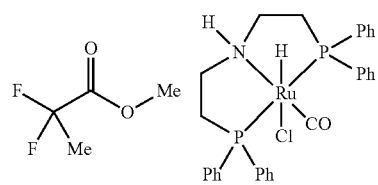

The inside of the reaction vessel was replaced five times with hydrogen gas. The hydrogen pressure inside the reaction vessel was then set to 1.0 MPa. The resulting solution inside the reaction vessel was stirred for 9 hours at 36° C. It was confirmed by gas chromatographic analysis of the reaction completed solution that the conversion rate and the selectivity of β-fluoroalcohol of the following formula were 100% and 90.4%, respectively. Further, the optical purity of β-fluoroalcohol was 66.2% ee.

The inside of the reaction vessel was replaced five times with hydrogen gas. The hydrogen pressure inside the reaction vessel was then set to 1.0 MPa. The resulting solution inside the reaction vessel was stirred all night at 37° C. It was confirmed by gas chromatographic analysis of the reaction completed solution that the conversion rate and the selectivity of β-fluoroalcohol of the following formula were 92% and 98.9%, respectively.

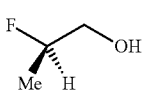

The reaction procedure and reaction results of the present example are indicated in the following scheme for reference purposes.

The reaction procedure and reaction results of the present example are indicated in the following scheme for reference purposes.

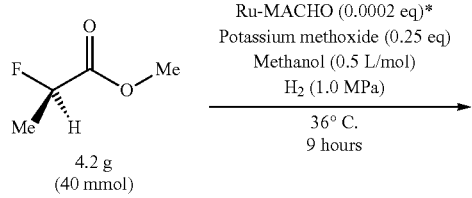 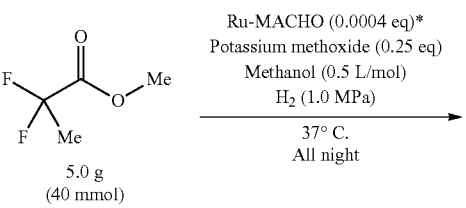

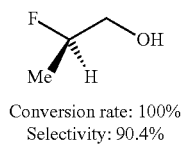 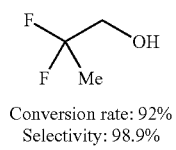

Conversion rate: 100%
Selectivity: 90.4%

Conversion rate: 92%
Selectivity: 98.9%

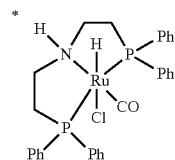 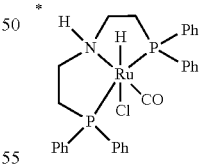

Example 4

A pressure-proof reaction vessel of stainless steel (SUS) was charged with 5.0 g (40 mmol, 1 eq) of α-fluoroester of the following formula, 10 mg (purity: 94.2%; 16 μmol, 0.0004 eq) of ruthenium complex of the following formula, 700 mg (10 mmol, 0.25 eq) of potassium methoxide and 20 mL (0.5 L/mol) of methanol.

Example 5

A pressure-proof reaction vessel of stainless steel (SUS) was charged with 4.8 g (40 mmol, 1 eq) of α-fluoroester of the following formula, 13 mg (purity: 94.2%; 20 μmol, 0.0005 eq) of ruthenium complex of the following formula, 540 mg (10 mmol, 0.25 eq) of sodium methoxide and 20 mL (0.5 L/mol) of methanol.

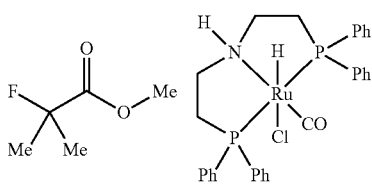 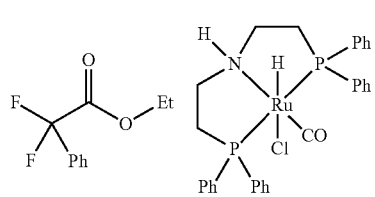

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by gas chromatographic analysis of the reaction completed solution that the conversion rate and the selectivity of β-fluoroalcohol of the following formula were 98% and 84.2%, respectively.

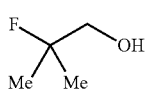

The reaction procedure and reaction results of the present example are indicated in the following scheme for reference purposes.

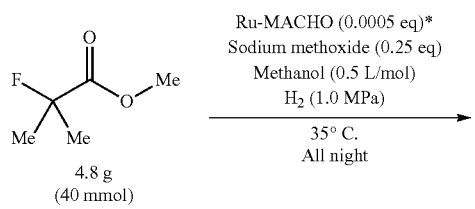

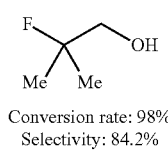

Conversion rate: 98%
Selectivity: 84.2%

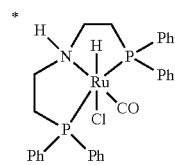

Example 6

A pressure-proof reaction vessel of stainless steel (SUS) was charged with 4.0 g (20 mmol, 1 eq) of α-fluoroester of the following formula, 4.3 mg (purity: 94.2%; 6.7 μmol, 0.0003 eq) of ruthenium complex of the following formula, 270 mg (5.0 mmol, 0.25 eq) of sodium methoxide and 10 mL (0.5 L/mol) of methanol.

The inside of the reaction vessel was replaced five times with hydrogen gas. The hydrogen pressure inside the reaction vessel was then set to 1.0 MPa. The resulting solution inside the reaction vessel was stirred all night at 40° C. It was confirmed by gas chromatographic analysis of the reaction completed solution that the conversion rate and the selectivity of β-fluoroalcohol of the following formula were 100% and 98.2%, respectively.

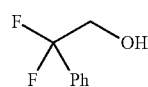

The reaction procedure and reaction results of the present example are indicated in the following scheme for reference purposes.

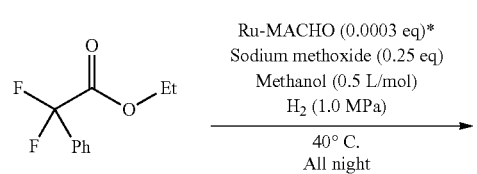

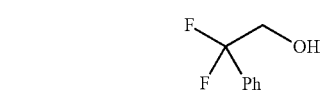

Conversion rate: 100%
Selectivity: 98.2%

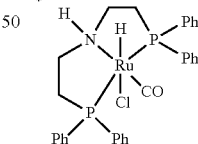

Example 7

A pressure-proof reaction vessel of stainless steel (SUS) was charged with 74 g (450 mmol, 1 eq) of α-fluoroester (E-configuration:Z-configuration=95:5) of the following formula, 120 mg (purity: 94.2%; 180 μmol, 0.0004 eq) of ruthenium complex of the following formula, 6.1 g (110 mmol, 0.25 eq) of sodium methoxide and 230 mL (0.5 L/mol) of methanol.

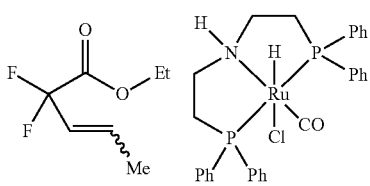

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by gas chromatographic analysis of the reaction completed solution that the conversion rate and the selectivity of β-fluoroalcohol (E-configuration:Z-configuration=95:5) of the following formula were 100% and 99.3%, respectively.

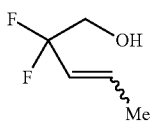

The reaction procedure and reaction results of the present example are indicated in the following scheme for reference purposes.

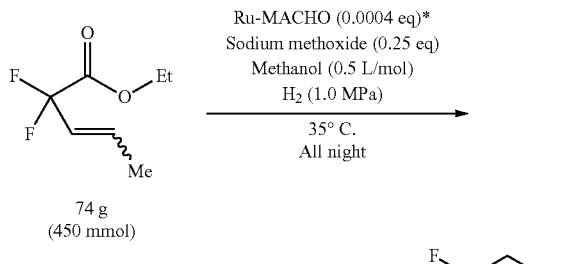

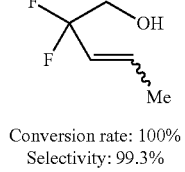

Conversion rate: 100%
Selectivity: 99.3%

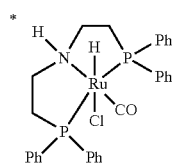

The above reaction operation was repeated twice to obtain the reaction completed solution equivalent to 490 mmol of α-fluoroester. The reaction completed solution was admixed with 7.4 g (120 mmol, 0.25 eq) of acetic acid. The admixed solution was directly subjected to distillation (oil bath temperature: ~63° C., vacuum degree: ~1.6 kPa) so that the target compound was recovered in the form of a methanol solution thereof. The distillation residue (i.e. the solid matter containing the target compound and sodium acetate) was washed by stirring with 240 mL of diisopropyl ether and filtered out. The resulting solid matter was further washed with a small amount of diisopropyl ether. The target compound was thus recovered in the form of a diisopropyl ether solution thereof. The above recovered solutions were combined and subjected to distillation separation (theoretical plate number: 4, distillation temperature: 60° C., 3.0 to 2.6 kPa), thereby yielding 46 g of β-fluoroalcohol of the above formula. The yield of β-fluoroalcohol was 77%. The gas chromatographic purity of β-fluoroalcohol was 99.6%. The $^1$H- and $^{19}$F-NMR measurement results of β-fluoroalcohol are indicated below.

[E-Configuration]

$^1$H-NMR (reference material: Me$_4$Si, deuterated solvent: CDCl$_3$) δ ppm; 1.80 (m, 3H), 3.72 (m, 2H), 5.63 (m, 1H), 6.19 (m, 1H). The proton of OH group was unidentified.

$^{19}$F-NMR (reference material: C$_6$F$_6$, deuterated solvent: CDCl$_3$) δ ppm; 55.96 (m, 2F).

[Z-Configuration]

$^1$H-NMR (reference material: Me$_4$Si, deuterated solvent: CDCl$_3$) δ ppm; 1.86 (m, 3H), 3.72 (m, 2H), 5.51 (m, 1H), 5.96 (m, 1H). The proton of OH group was unidentified.

$^{19}$F-NMR (reference material: C$_6$F$_6$, deuterated solvent: CDCl$_3$) δ ppm; 59.57 (m, 2F).

Example 8

A pressure-proof reaction vessel of stainless steel (SUS) was charged with 38 g (250 mmol, 1 eq) of α-fluoroester of the following formula, 64 mg (purity: 94.2%; 100 μmol, 0.0004 eq) of ruthenium complex of the following formula, 3.4 g (63 mmol, 0.25 eq) of sodium methoxide and 250 mL (0.5 L/mol) of methanol.

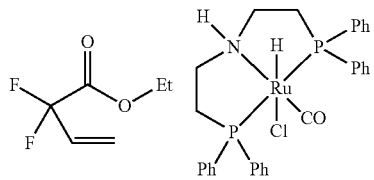

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by $^{19}$F-NMR analysis of the reaction completed solution that the conversion rate and the selectivity of β-fluoroalcohol of the following formula were 100% and 98.0%, respectively.

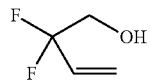

The reaction procedure and reaction results of the present example are indicated in the following scheme for reference purposes.

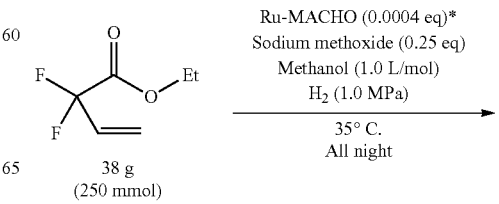

-continued

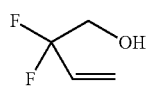

Conversion rate: 100%
Selectivity: 98.0%

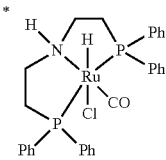

The above reaction operation was repeated twice to obtain the reaction completed solution equivalent to 470 mmol of α-fluoroester. The reaction completed solution was admixed with 7.1 g (120 mmol, 0.25 eq) of acetic acid and an appropriate amount of methoquinone (polymerization inhibitor). The admixed solution was directly subjected to distillation (oil bath temperature: ~63° C., vacuum degree: ~7.9 kPa) so that the target compound was recovered in the form of a methanol solution thereof. The distillation residue (i.e. the solid matter containing the target compound and sodium acetate) was washed by stirring with 400 mL of diisopropyl ether and filtered out. The resulting solid matter was further washed with a small amount of diisopropyl ether. The target compound was thus recovered in the form of a diisopropyl ether solution thereof. The above recovered solutions were combined and subjected to distillation separation (theoretical plate number: 4, distillation temperature: 57 to 62° C., 13 to 12 kPa), thereby yielding 40 g of β-fluoroalcohol of the above formula. The yield of β-fluoroalcohol was 78%. The gas chromatographic purity of β-fluoroalcohol was 98.9%. The $^1$H- and $^{19}$F-NMR measurement results of β-fluoroalcohol are indicated below.

$^1$H-NMR (reference material: Me$_4$Si, deuterated solvent: CDCl$_3$) δ ppm; 2.21 (br, 1H), 3.81 (t, 2H), 5.55 (d, 1H), 5.74 (m, 1H), 5.97 (m, 1H).

$^{19}$F-NMR (reference material: C$_6$F$_6$, deuterated solvent: CD$_3$OD) δ ppm; 55.44 (m, 2F).

Example 9

A pressure-proof reaction vessel of stainless steel (SUS) was charged with 6.0 g (30 mmol, 1 eq) of α-fluoroester of the following formula, 6.5 mg (purity: 94.2%; 10 μmol, 0.0003 eq) of ruthenium complex of the following formula, 406 mg (7.5 mmol, 0.25 eq) of sodium methoxide and 15 mL (0.5 L/mol) of methanol.

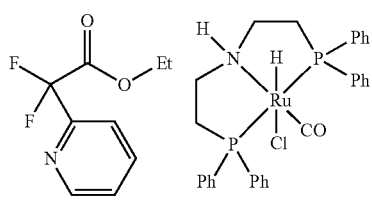

The inside of the reaction vessel was replaced five times with hydrogen gas. The hydrogen pressure inside the reaction vessel was then set to 1.0 MPa. The resulting solution inside the reaction vessel was stirred all night at 38° C. It was confirmed by gas chromatographic analysis of the reaction completed solution that the conversion rate and the selectivity of β-fluoroalcohol of the following formula were 100% and 98.2%, respectively.

The reaction procedure and reaction results of the present example are indicated in the following scheme for reference purposes.

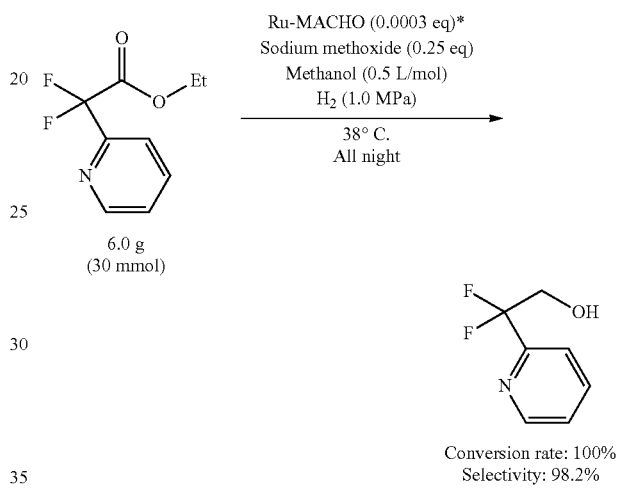

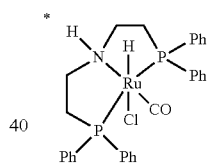

Conversion rate: 100%
Selectivity: 98.2%

Example 10

A pressure-proof reaction vessel of stainless steel (SUS) was charged with 6.4 g (30 mmol, 1 eq) of α-fluoroester of the following formula, 6.5 mg (purity: 94.2%; 10 μmol, 0.0003 eq) of ruthenium complex of the following formula, 406 mg (7.5 mmol, 0.25 eq) of sodium methoxide and 15 mL (0.5 L/mol) of methanol.

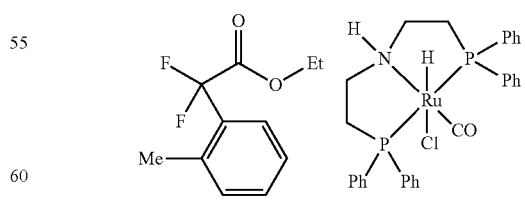

The inside of the reaction vessel was replaced five times with hydrogen gas. The hydrogen pressure inside the reaction vessel was then set to 1.0 MPa. The resulting solution inside the reaction vessel was stirred all night at 38° C. It was confirmed by gas chromatographic analysis of the reaction completed solution that the conversion rate and the selectivity of β-fluoroalcohol of the following formula were 98.0% and 98.0%, respectively.

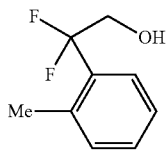 [SMILES: Cc1ccccc1C(F)(F)CO]

The reaction procedure and reaction results of the present example are indicated in the following scheme for reference purposes.

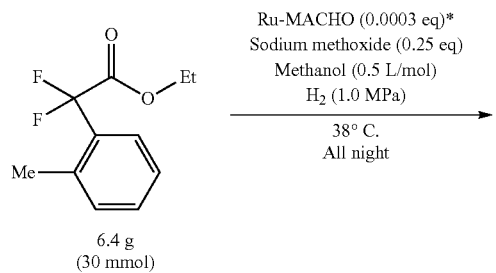

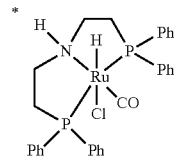

The ¹H- and ¹⁹F-NMR measurement results of β-fluoroalcohol are indicated below. ¹H-NMR (reference material: Me₄Si, deuterated solvent: CDCl₃) δ ppm; 1.90 (br, 1H), 2.52 (t, 3H), 4.06 (t, 2H), 7.29 (m, 2H), 7.39 (dd, 1H) 7.54 (d, 1H).

¹⁹F-NMR (reference material: C₆F₆, deuterated solvent: CDCl₃) δ ppm; 57.04 (t, 2F).

Example 11

A pressure-proof reaction vessel of stainless steel (SUS) was charged with 3.6 g (20 mmol, 1 eq) of α-fluoroester of the following formula, 4.3 mg (purity: 94.2%; 6.7 µmol, 0.0003 eq) of ruthenium complex of the following formula, 162 mg (3.0 mmol, 0.15 eq) of sodium methoxide and 20 mL (1.0 L/mol) of methanol.

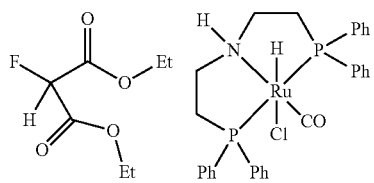

The inside of the reaction vessel was replaced five times with hydrogen gas. The hydrogen pressure inside the reaction vessel was then set to 1.0 MPa. The resulting solution inside the reaction vessel was stirred all night at 38° C. It was confirmed by gas chromatographic analysis of the reaction completed solution that the conversion rate and the selectivity of β-fluoroalcohol of the following formula were 99.6% and 74.2%, respectively.

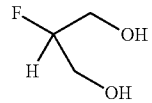

The reaction procedure and reaction results of the present example are indicated in the following scheme for reference purposes.

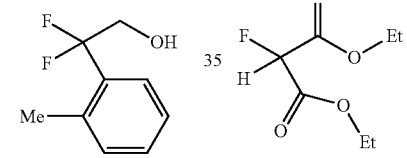

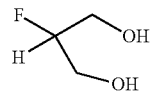

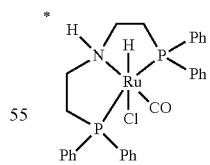

Example 12

A pressure-proof reaction vessel of stainless steel (SUS) was charged with 77 mg (purity: 94.2%; 0.12 mmol, 0.0003 eq) of ruthenium complex of the following formula, 1.6 g (30 mmol, 0.06 eq) of sodium methoxide and 240 mL (0.5 L/mol) of methanol.

23

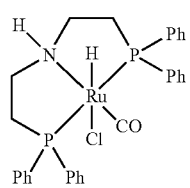

The inside of the reaction vessel was replaced five times with hydrogen gas. The hydrogen pressure inside the reaction vessel was then set to 1.0 MPa. Into the resulting solution inside the reaction vessel, a mixed solution of 51 g (480 mmol, 1 eq, optical purity: 97.3% ee) of α-fluoroester of the following formula in 240 mL (0.5 L/mol) of methanol was dropped over 14 hours at 36° C.

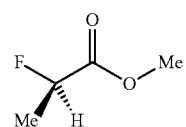

This solution was stirred for 11 hours at the same temperature as above. It was confirmed by gas chromatographic analysis of the reaction completed solution that the conversion rate and the selectivity of β-fluoroalcohol of the following formula were 98.5% and 98.8%, respectively. Further, the optical purity of β-fluoroalcohol was 95.0% ee.

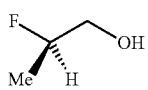

The reaction procedure and reaction results of the present example are indicated in the following scheme for reference purposes.

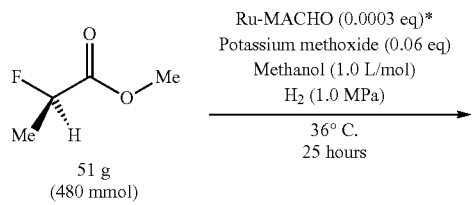

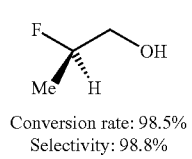

Conversion rate: 98.5%
Selectivity: 98.8%

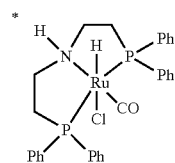

24

Example 13

A pressure-proof reaction vessel of stainless steel (SUS) was charged with 3.6 g (20 mmol, 1 eq) of α-fluoroester of the following formula, 6.5 mg (purity: 94.2%; 10 μmol, 0.0005 eq) of ruthenium complex of the following formula, 270 mg (5.0 mmol, 0.25 eq) of sodium methoxide and 10 mL (0.5 L/mol) of methanol.

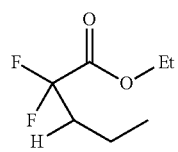

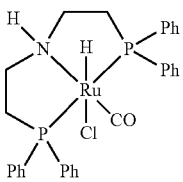

The inside of the reaction vessel was replaced five times with hydrogen gas. The hydrogen pressure inside the reaction vessel was then set to 2.0 MPa. The resulting solution inside the reaction vessel was stirred all night at 38° C. It was confirmed by gas chromatographic analysis of the reaction completed solution that the conversion rate and the selectivity of β-fluoroalcohol of the following formula were 100% and 99.6%, respectively.

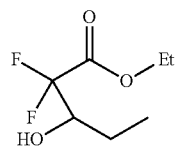

The reaction procedure and reaction results of the present example are indicated in the following scheme for reference purposes.

Conversion rate: 100%
Selectivity: 99.6%

-continued

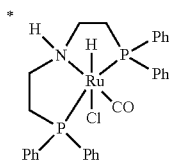

Comparative Example 1

A pressure-proof reaction vessel of stainless steel (SUS) was charged with 5.0 g (40 mmol, 1 eq) of α-fluoroester of the following formula, 30 mg (40 μmol, 0.001 eq) of ruthenium complex of the following formula, 1.1 g (9.8 mmol, 0.25 eq) of potassium tert-butoxide and 20 mL (0.5 L/mol) of tetrahydrofuran.

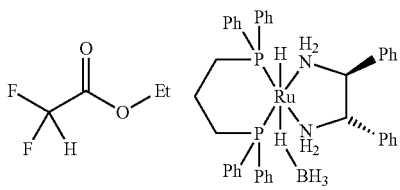

The inside of the reaction vessel was replaced five times with hydrogen gas. The hydrogen pressure inside the reaction vessel was then set to 3.8 MPa. The resulting solution inside the reaction vessel was stirred all night at 100° C. It was confirmed by gas chromatographic analysis of the reaction completed solution that the conversion rate and the selectivity of β-fluoroalcohol of the following formula were 100% and 93.8%, respectively.

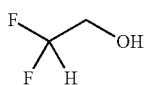

It was impossible to obtain the same level results as those of Example 1 (conversion rate: 100%, target compound selectivity: 100%) even by changing the ester moiety of α-fluoroester to methyl ester, changing the base to sodium methoxide, changing the reaction solvent to methanol, using double the amount of methanol, setting the reaction temperature to 40° C. or any combination thereof in Comparative Example 1. For reference purposes, the reaction procedure and reaction results of the present comparative example are indicated in the following scheme.

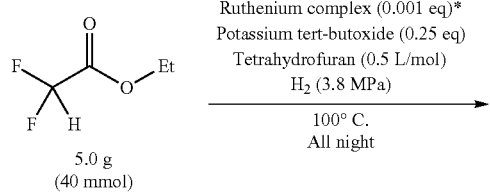

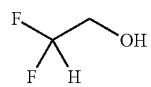

Conversion rate: 100%
Selectivity: 93.8%

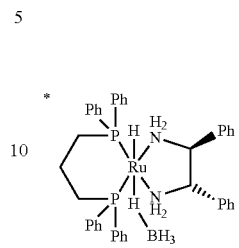

Comparative Example 2

A pressure-proof reaction vessel of stainless steel (SUS) was charged with 3.0 g (40 mmol, 1 eq) of methyl acetate of the following formula, 5.2 mg (purity: 94.2%, 8.0 μmol, 0.0002 eq) of ruthenium complex of the following formula, 700 mg (10 mmol, 0.25 eq) of potassium methoxide and 20 mL (0.5 L/mol) of methanol.

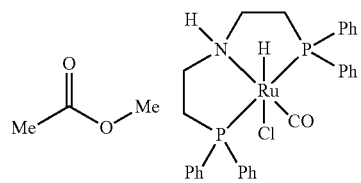

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by gas chromatographic analysis of the reaction completed solution that the conversion rate and the selectivity of β-fluoroalcohol of the following formula were 18% and 94.4%, respectively.

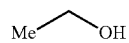

The reaction procedure and reaction results of the present comparative example are indicated in the following scheme for reference purposes.

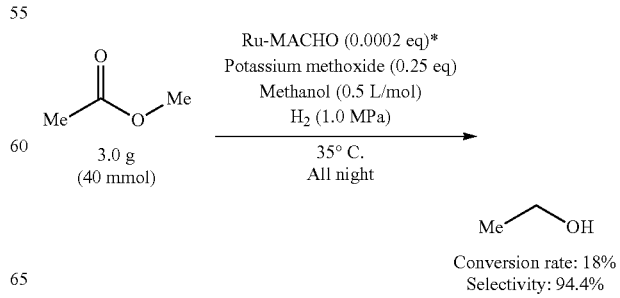

Conversion rate: 18%
Selectivity: 94.4%

-continued

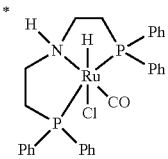

INDUSTRIAL APPLICABILITY

The β-fluoroalcohols produced by the production method according to the present invention are usable as intermediates for pharmaceutical and agrichemical products.

The invention claimed is:

1. A method for producing a β-fluoroalcohol of the general formula [3], comprising: performing a reaction of an α-fluoroester of the general formula [1] with hydrogen gas ($H_2$) in the presence of a ruthenium complex of the general formula [2]

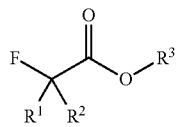
[1]

where $R^1$ and $R^2$ each independently represent a hydrogen atom, a halogen atom, an alkyl group, a substituted alkyl group, an aromatic ring group, a substituted aromatic ring group, an alkoxycarbonyl group or a substituted alkoxycarbonyl group; and $R^3$ represents an alkyl group or a substituted alkyl group

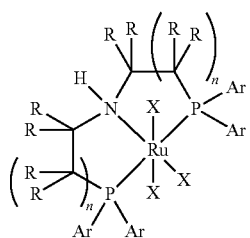
[2]

where R each independently represent a hydrogen atom, an alkyl group, a substituted alkyl group, an aromatic ring group or a substituted aromatic ring group; Ar each independently represent an aromatic ring group or a substituted aromatic ring group; X each independently represent a ligand having a formal charge of −1 or 0 (wherein a sum of formal charges of three X is −2); and n each independently represent an integer of 1 or 2

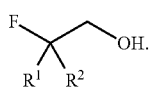
[3]

2. The method according to claim 1, wherein the reaction is performed in the presence of a base.

3. The method according to claim 2, wherein the ruthenium complex of the general formula [2] is a ruthenium complex of the general formula [4]

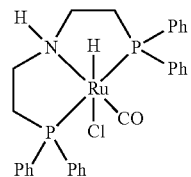
[4]

where Ph represent a phenyl group.

4. The method according to claim 1, wherein the α-fluoroester of the general formula [1] is an α-fluoroester of the general formula [5]; and wherein the β-fluoroalcohol of the general formula [3] is a β-fluoroalcohol of the general formula [6]

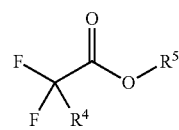
[5]

where $R^4$ represents a hydrogen atom, an alkyl group, a substituted alkyl group, an aromatic ring group or a substituted aromatic ring group; and $R^5$ represents an alkyl group

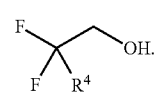
[6]

5. The method according to claim 1, wherein the α-fluoroester of the general formula [1] is an α-fluoroester of the general formula [7]; and wherein the β-fluoroalcohol of the general formula [3] is a β-fluoroalcohol of the general formula [8]

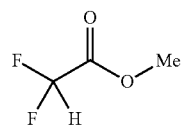
[7]

where Me represents a methyl group

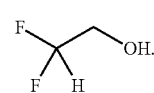
[8]

6. The method according to claim 1, wherein the reaction is performed at a hydrogen pressure of 3 MPa or lower.

7. The method according to claim 6, wherein the reaction is performed at a hydrogen pressure of 2 MPa or lower.

8. The method according to claim 7, wherein the reaction is performed at a hydrogen pressure of 1 MPa or lower.

* * * * *